(12) United States Patent
Masson et al.

(10) Patent No.: US 10,092,540 B2
(45) Date of Patent: *Oct. 9, 2018

(54) METHOD OF TREATMENT OF A MUCOPOLYSACCHARIDOSIS

(71) Applicant: INVENTIVA, Daix (FR)

(72) Inventors: Philippe Masson, Hauteville-les-Dijon (FR); Jean-Louis Junien, Sevres (FR); Mireille Tallandier, Bretigny (FR)

(73) Assignee: INVENTIVA, Daix (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/420,135

(22) Filed: Jan. 31, 2017

(65) Prior Publication Data

US 2017/0189375 A1 Jul. 6, 2017

Related U.S. Application Data

(63) Continuation-in-part of application No. 14/506,239, filed on Oct. 3, 2014, now Pat. No. 9,561,246.

(30) Foreign Application Priority Data

Oct. 4, 2013 (FR) ..................................... 13 59659

(51) Int. Cl.
*A61K 31/382* (2006.01)
*A61K 9/00* (2006.01)

(52) U.S. Cl.
CPC .......... *A61K 31/382* (2013.01); *A61K 9/0053* (2013.01)

(58) Field of Classification Search
None
See application file for complete search history.

(56) References Cited

U.S. PATENT DOCUMENTS 5,169,838 A 12/1992 Samreth et al.

FOREIGN PATENT DOCUMENTS

EP 0 421 829 4/1991

OTHER PUBLICATIONS

Weinstein et al. Connective Tissue Research, Early Online: 1-11. 2011 (Year: 2011).*
Neufeld et al., "The Mucopolysaccharidoses", The Metabolic Basis of Inherited Diseases, 1989, 6th Edition, Chapter 61, pp. 1565-1587.
Weinstein et al., "β-D-Xylosides Stimulates GAG Synthesis in Chondrocyte Cultures Due to Elevation of the Extracellular GAG Domains, Accompanied by the Depletion of the Intra-pericellular GAG Pools, with Alterations in the GAG Profiles", Connective Tissue Research, Early Online: 1-11, 2011.
Myers et al., "Characterization of Total . . . Aspirin or Enoxaparin", Journal of Clinical Pharmacology, vol. 48, No. 10, Oct. 10, 2008, pp. 1158-1170, XP002719465.
European Search Report dated Jan. 30, 2014, with partial translation.
Harmatz et al. In Journal of Pediatrics 2006; 148:533-539.
Schuchman et al. In PLOS One 8(1): e54459 (published: Jan. 24, 2013).

* cited by examiner

*Primary Examiner* — Dennis Heyer
(74) *Attorney, Agent, or Firm* — Clark & Brody

(57) ABSTRACT

The present invention relates to the use of 4-methyl-2-oxo-2H-1-benzopyran-7-yl-5-thio-β-D-xylopyranoside in the treatment of a mucopolysaccharidosis such as type I mucopolysaccharidosis.

17 Claims, 3 Drawing Sheets

METHOD OF TREATMENT OF A MUCOPOLYSACCHARIDOSIS

This application is a Continuation-in-Part of U.S. Ser. No. 14/506,239 filed on Oct. 3, 2014, which is incorporated in its entirety by reference into this CIP application.

FIELD OF THE INVENTION

The present invention relates to the use of odiparcil, or of a pharmaceutical composition containing this compound, in the treatment of a mucopolysaccharidosis.

BACKGROUND OF THE INVENTION

Mucopolysaccharidoses (MPSs) are degenerative genetic diseases linked to an enzymatic defect. In particular, MPSs are caused by the deficiency or the inactivity of lysosomal enzymes which catalyze the gradual metabolism of complex sugar molecules called glycosaminoglycans (GAGs). These enzymatic deficiencies cause an accumulation of GAGs in the cells, the tissues and, in particular, the cell lysosomes of affected subjects, leading to permanent and progressive cell damage which affects the appearance, the physical capacities, the organ function and, in most cases, the mental development of affected subjects.

Eleven distinct enzymatic defects have been identified, corresponding to seven distinct clinical categories of MPS. Each MPS is characterized by a deficiency or inactivity of one or more enzymes which degrade mucopolysaccharides, namely heparan sulfate, dermatan sulfate, chondroitin sulfate and keratan sulfate.

MPS I is divided into three subtypes based on severity of symptoms. All three types result from an absence of, or insufficient levels of, the enzyme alpha-L-iduronidase.

Children born to an MPS I parent carry the defective gene.

MPS I H (also called Hurler syndrome or α-L-iduronidase deficiency), is the most severe of the MPS I subtypes. Developmental delay is evident by the end of the first year, and patients usually stop developing between ages 2 and 4. This is followed by progressive mental decline and loss of physical skills. Language may be limited due to hearing loss and an enlarged tongue. In time, the clear layers of the cornea become clouded and retinas may begin to degenerate. Carpal tunnel syndrome (or similar compression of nerves elsewhere in the body) and restricted joint movement are common. Affected children may be quite large at birth and appear normal but may have inguinal (in the groin) or umbilical (where the umbilical cord passes through the abdomen) hernias. Growth in height may be faster than normal but begins to slow before the end of the first year and often ends around age 3. Many children develop a short body trunk and a maximum stature of less than 4 feet. Distinct facial features (including flat face, depressed nasal bridge, and bulging forehead) become more evident in the second year. By age 2, the ribs have widened and are oar-shaped. The liver, spleen, and heart are often enlarged. Children may experience noisy breathing and recurring upper respiratory tract and ear infections. Feeding may be difficult for some children, and many experience periodic bowel problems. Children with Hurler syndrome often die before age 10 from obstructive airway disease, respiratory infections, and cardiac complications.

MPS I S, Scheie syndrome, is the mildest form of MPS 1. Symptoms generally begin to appear after age 5, with diagnosis most commonly made after age 10. Children with Scheie syndrome have normal intelligence or may have mild learning disabilities; some may have psychiatric problems. Glaucoma, retinal degeneration, and clouded corneas may significantly impair vision. Other problems include carpal tunnel syndrome or other nerve compression, stiff joints, claw hands and deformed feet, a short neck, and aortic valve disease. Some affected individuals also have obstructive airway disease and sleep apnea. Persons with Scheie syndrome can live into adulthood.

MPS I H-S, Hurler-Scheie syndrome, is less severe than Hurler syndrome alone. Symptoms generally begin between ages 3 and 8. Children may have moderate intellectual disability and learning difficulties. Skeletal and systemic irregularities include short stature, marked smallness in the jaws, progressive joint stiffness, compressed spinal cord, clouded corneas, hearing loss, heart disease, coarse facial features, and umbilical hernia. Respiratory problems, sleep apnea, and heart disease may develop in adolescence. Some persons with MPS I H-S need continuous positive airway pressure during sleep to ease breathing. Life expectancy is generally into the late teens or early twenties.

MPS II, also known as Hunter syndrome, is caused by lack of the enzyme iduronate sulfatase. Hunter syndrome has two clinical subtypes and (since it shows X-linked recessive inheritance) is the only one of the mucopolysaccharidoses in which the mother alone can pass the defective gene to a son. The incidence of Hunter syndrome is estimated to be 1 in 100,000 to 150,000 male births.

Mucopolysaccharidosis type VI (MPS VI) or Maroteaux-Lamy disease is a lysosomal storage disease, of the mucopolysaccharidosis group, characterized by severe somatic involvement and an absence of psycho-intellectual regression. The prevalence of this rare mucopolysaccharidosis is between 1/250 000 and 1/600 000 births. In the severe forms, the first clinical manifestations occur between 6 and 24 months and are gradually accentuated: facial dysmorphia (macroglossia, mouth constantly half open, thick features), joint limitations, very severe dysostosis multiplex (platyspondyly, kyphosis, scoliosis, pectus carinatum, genu valgum, long bone deformation), small size (less than 1.10 m), hepatomegaly, heart valve damage, cardiomyopathy, deafness, corneal opacities. Intellectual development is usually normal or virtually normal, but the auditory and ophthalmological damage can cause learning difficulties. The symptoms and the severity of the disease vary considerably from one patient to the other and intermediate forms, or even very moderate forms also exist (spondyloepiphyseal-metaphyseal dysplasia associated with cardiovascular involvement). Like the other mucopolysaccharidoses, Maroteaux-Lamy disease is linked to the defect of an enzyme of mucopolysaccharide metabolism, in the case in point N-acetylgalactosamine-4-sulfatase (also called arylsulfatase B). This enzyme metabolizes the sulfate group of dermatan sulfate (Neufeld et al.: "The mucopolysaccharidoses" The Metabolic Basis of Inherited Diseases, eds. Scriver et al, New York, McGraw-Hill, 1989, p. 1565-1587). This enzymatic defect blocks the gradual degradation of dermatan sulfate, thereby leading to an accumulation of dermatan sulfate in the lysosomes of the storage tissues. At the current time, there is just one medicament authorized for the treatment of this disease: Naglazyme® (recombinant human galsulfase), the cost of which is extremely high (in the United States, it is about $ 350 000 per year). An alternative to this treatment is bone marrow allograft.

Mucopolysaccharidosis type VII (MPS VII) or Sly disease is a very rare lysosomal storage disease of the mucopolysaccharidosis group. The symptomology is extremely heterogeneous: antenatal forms (nonimmune fetoplacental anasarca), severe neonatal forms (with dysmorphia, hernias, hepatosplenomegaly, club feet, dysostosis, significant hypotonia and neurological problems evolving to retarded growth and a profound intellectual deficiency in the event of survival) and very moderate forms discovered at adolescence or even at adult age (thoracic kyphosis). The disease is due to a defect in beta-D-glucuronidase, responsible for accumulation, in the lysosomes, of various glycosaminoglycans: dermatan sulfate, heparan sulfate and chondroitin sulfate. There is at the current time no effective treatment for this disease.

There is therefore clearly a need to provide subjects suffering from MPS type I, II, VI and VII with a drug treatment, and in the case of MPS type VI, an alternative treatment not derived from biotechnology.

Odiparcil (4-methyl-2-oxo-2H-1-benzopyran-7-yl-5-thio-β-D-xylopyranoside; CAS 137215-12-4) belongs to the thioxyloside family. This compound, described in patent application EP-A-0 421 829, corresponds to the formula:

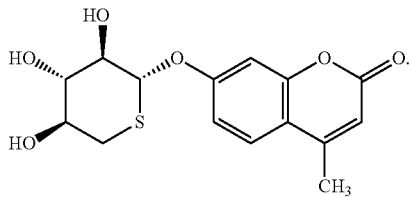 [SMILES: Cc1cc(=O)oc2cc(O[C@@H]3SC[C@@H](O)[C@H](O)[C@H]3O)ccc12]

This compound was the subject of a clinical development (phases 1 and 2) in the treatment of thrombosis at the end of the 1990s and at the beginning of the 2000s. Its mechanism of action can be summarized in the following way: Odiparcil behaves as a substrate for an enzyme, GT1 (galactosyl transferase 1), which initiates the synthesis of GAG chains toward the dermatan sulfate/chondroitin sulfate pathway. These GAGs are cell constituents as proteoglycans, where they are linked to the core-protein moiety at serine residues through a linkage region composed of xylose-galactose-galactose. Proteoglycans are widely distributed in tissues, especially connective tissues, are major constituents of cell membranes and cell extracellular matrix. They have varied biological roles, ranging from the control of coagulation (heparin/heparan and dermatan sulfate secreted into the circulation), structural and physical organisation of cartilages to the regulation of growth factors (beta-glycan).

It has now been noted, and this is the subject of the present invention, that odiparcil makes it possible to increase total GAG synthesis at the extracellular level and, by the same token, will contribute to reducing the intracellular GAG load by acting as a "decoy" making the residual activity of N-acetylgalactosamine-4-sulfatase more effective. It is thus possible to envision the treatment of MPS type I, II, VI and VII owing to the decrease in GAG accumulation at the intracellular level.

SUMMARY OF THE INVENTION

The invention relates to a method of treatment of a mucopolysaccharidosis type I or II, which comprises administering to a subject in need thereof odiparcil or a pharmaceutical composition containing such compound.

DETAILED DESCRIPTION OF THE INVENTION

Figure 1:
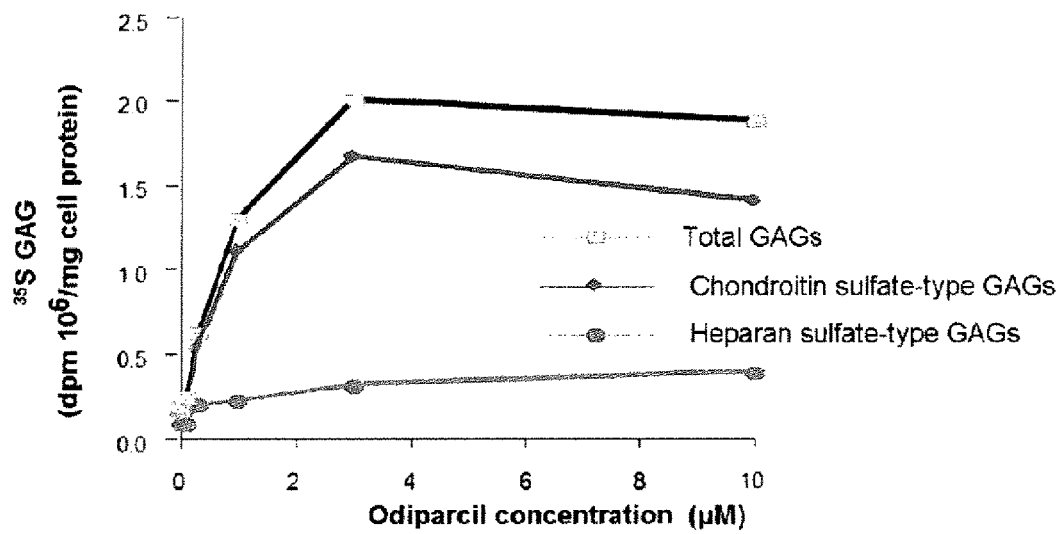
FIG. 1 shows the effect of odiparcil on GAG levels in bovine aortic endothelial cells.

According to a first aspect, the invention relates to a method of treatment of a mucopolysaccharidosis type I or II, which comprises administering to a subject in need thereof a therapeutically effective amount of odiparcil.

Odiparcil and the process for obtaining it are described in patent application EP-A-0 421 829.

In the context of the present invention, the term "odiparcil" denotes the "β-D-xylopyranoside" form.

In one embodiment, odiparcil used in the context of the invention is at least 60%, preferably at least 70%, at least 80%, at least 90%, at least 95%, at least 98% or at least 99% in the D-configuration. In this embodiment, the odiparcil is preferably in β-anomer form.

In another embodiment, odiparcil used in the context of the invention is at least 60%, preferably at least 70%, at least 80%, at least 90%, at least 95%, at least 98% or at least 99% in the β-anomer form.

Advantageously, odiparcil is administered in a proportion of approximately 100 mg to approximately 5000 mg per day. For example, approximately 100, 250, 300, 375, 400, 500, 750, 800, 1000, 1500, 2000, 3000, 4000 or 5000 mg of odiparcil are administered daily.

In one embodiment, at least approximately 0.1 mg to approximately 70 mg of odiparcil per kg of bodyweight of the patient are administered daily. For example, at least approximately 1 or 2 mg, to approximately 5, 10, 15, 20, 25, 30, 35, 40, 45, 50, 55, 60, 65 or 70 mg of odiparcil per kg of bodyweight of the patient are administered daily.

In one embodiment, odiparcil is administered once or twice per day (for example, every 10 to 12 hours). Thus, the daily doses mentioned above can be divided up for a twice daily (bid) administration, for example a daily dose of 1000 mg will be administered in a proportion of two doses of 500 mg each. It is understood that each dose may consist of one or more pharmaceutical forms, for example a dose of 500 mg may consist of two pharmaceutical forms of 250 mg each.

In one embodiment, odiparcil is administered in a fasted state (i.e. on an empty stomach, for example at least 1 h before eating or more than 2 h after eating). In another embodiment, odiparcil is administered during a food intake (i.e. at the same time as or just before eating a meal, for example approximately 20 to 30 min before a meal or within 5 min following the end of a meal).

In one embodiment, odiparcil is formulated in a pharmaceutical composition containing one or more pharmaceutically acceptable excipients, according to techniques well known to those skilled in the art, for instance those described in the book "Remington, The Science and Practice of Pharmacy, 21st Edition, Lippincott Williams & Wilkins, 2006".

Thus, according to a second aspect, the invention relates to a method of treatment of a mucopolysaccharidosis type I or II, which comprises administering to a subject in need thereof a pharmaceutical composition containing a therapeutically effective amount of odiparcil and one or more pharmaceutically acceptable excipients.

The pharmaceutical composition may be in any form suitable for the desired route of administration. This administration may be per os, lingual, sublingual, oral, rectal, topical, intravenous, intra-arterial, subcutaneous, intranasal, transdermal, intra-muscular or intraperitoneal.

In one embodiment, the pharmaceutical composition contains approximately 100 to 1000 mg of odiparcil, for example 100, 125, 150, 250, 375, 400, 500 or 1000 mg of odiparcil.

In one embodiment, the pharmaceutical composition is administered by the injectable route, and comprises a vehicle which is typically a sterile aqueous solution sometimes containing, in addition to the water, one or more ingredients such as sugars, preservatives, salts, buffers, etc. The injectable suspensions may comprise a suspending agent and a given liquid vehicle.

In one embodiment, the pharmaceutical composition is administered orally. Suitable oral pharmaceutical forms include solid and liquid formulations. When the pharmaceutical composition is a solid formulation (such as, for example, gelatin capsules, tablets, dry powders), useful excipients include, in particular, diluents, lubricants, binders, disintegrating agents, fillers, etc. The solid formulations may be coated or uncoated; when they are coated, the coating may be enteric or nonenteric. When the pharmaceutical composition is a liquid formulation (such as, for example, an elixir or a syrup), the useful excipients include, for example, water, glycols, a saline solution, alcohols, flavoring agents, etc.

Advantageously, the pharmaceutical composition is a tablet. Such a composition is prepared in one or more steps, comprising the mixing of the various constituents until a homogeneous mixture is obtained, and the compressing of the mixture so as to obtain a tablet. In one embodiment, the composition is prepared by means of a wet granulation process, which is a technique well known to those skilled in the art. For example, odiparcil, all or part of the diluent, the binder and a sufficient amount of granulating fluid (such as water) are combined, granulated, dried and ground so as to form granules. The granules are then optionally combined with the rest of the constituents and the mixture is compressed. The tablets advantageously comprise approximately 5% to approximately 90% of odiparcil, relative to the total weight of the tablet.

According to a third aspect, the invention relates to a method for treating mucopolysaccharidosis type VI or VII, in particular Maroteaux-Lamy disease, which consists in administering, to a subject in need thereof, a therapeutically effective amount of odiparcil or of a pharmaceutical composition containing this compound. In one embodiment, the daily dosage regimen of odiparcil and the pharmaceutical composition are as defined above.

The invention is illustrated by the examples below.

Example 1: Results Obtained on Cells in Culture

1) Bovine Aortic Endothelial Cells

Bovine aortic endothelial cells (ECACC 92010601), cultured in 6-well plates, were incubated for 24 h in the presence of $^{35}$S sodium sulfate (10 µci/ml) and of odiparcil solubilized in DMSO at various concentrations (1-10 µM; 0.1% final concentration of DMSO). The culture supernatants were recovered and the cell layers were rinsed with phosphate buffer (PBS). The culture supernatants and the rinsing solutions were combined in tubes. A solution of unlabeled dermatan sulfate (200 µg) was then added in order to serve as an entraining agent. The unincorporated $^{35}$S was then removed by gel filtration on Sephadex G25 columns, the GAGs being eluted in the column exclusion fraction (V0). A solution of cetylpyridinium chloride (0.1% final concentration) was added to the eluent in order to precipitate the GAGs for 24 h at room temperature. The samples were then centrifuged and the supernatant was removed. The precipitate obtained was redissolved in 2 M magnesium chloride and the GAGs were precipitated with 5 volumes of 95% ethanol. After centrifugation, the alcoholic precipitates were redissolved in 0.9% sodium chloride and then the radioactivity was measured on an aliquot fraction after addition of scintillation fluid in counting vials.

In order to type the GAGs produced in the supernatants from cells in culture, the redissolved alcoholic precipitates were treated with chondroitinase ABC (*Proteus vulgaris*) in a proportion of 0.5 mU/µL, for 3 h at 37° C. After inactivation of the enzyme for 3 min at 100° C., the undigested GAGs were precipitated with 5 volumes of 95% ethanol, overnight at 4° C. After centrifugation, the alcoholic precipitates were redissolved in 0.9% sodium chloride and then the radioactivity was measured on an aliquot fraction after addition of scintillation fluid in counting vials.

GAGs of heparan sulfate type were treated with heparinase II (*Flavobacterium heparinum*) in a proportion of 4 mU/µl, for 12 h at 30° C. After inactivation of the enzyme for 3 min at 100° C., the undigested GAGs were precipitated with 5 volumes of 95% ethanol, overnight at 4° C. After centrifugation, the alcoholic precipitates were redissolved in 0.9% sodium chloride and then the radioactivity was measured on an aliquot fraction after addition of scintillation fluid in counting vials.

As can be seen in FIG. 1, odiparcil increases, in a dose-dependent manner, the level of $^{35}$S-labeled GAGs in the culture supernatant of bovine aortic endothelial cells. Furthermore, the enzymatic digestions suggest that the GAGs synthesized by the cells in culture are predominantly of chondroitin sulfate type.

2) Normal Human Fibroblasts

Normal human dermal fibroblasts (BIOAlternatives PF2) were cultured in 96-well plates for 24 h. The culture medium was then replaced with culture medium containing or not containing (control) odiparcil at various concentrations (1 µM, 3 µM, 10 µM) or the TGF-β reference at 10 ng/ml (positive control), and then the cells were incubated for 72 h with addition of the $^3$H-glucosamine radioactive label for evaluating total GAG synthesis. At the end of the incubation, a chaotropic buffer was added to the wells of the culture plates in order to lyse the fibroblasts. The total GAGs of the cell lysates were then purified by ion exchange chromatography (Q-Sepharose column). The radioactivity incorporated into the anionic fractions was measured by liquid scintillation.

Figure 2:
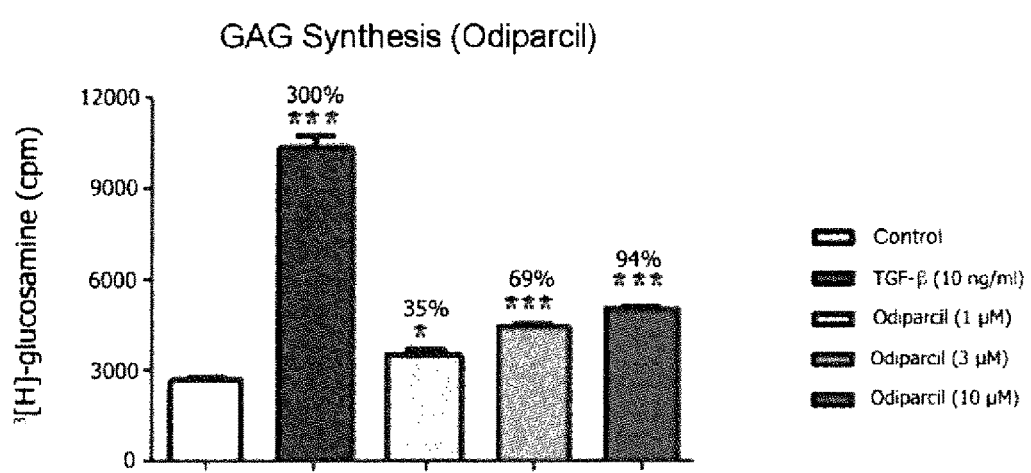
FIG. 2 shows the effect of odiparcil on GAG synthesis by normal human dermal fibroblasts.

As can be seen in FIG. 2, odiparcil stimulates, in a dose-dependent manner, total GAG synthesis by human dermal fibroblasts (+94% at 10 µM). The data were analyzed statistically by one-way analysis of variance, followed by a Dunnett's test (* $p<0.05$ vs control;  $p<0.01$ vs control; * $p<0.001$ vs control).

3) Human Fibroblasts from MPS I and MPS II Patients
a) Effect on Chondroitin Sulfate in Human Fibroblasts from MPS 1 Patients Human dermal fibroblasts (GM00034B fibroblast cells, isolated from an MPS I patient and GM00031 fibroblast cells, isolated from an unaffected donor) were obtained from the Coriell Institute for Medical Research. Cells were cultured in 96-well plates for 24 h. The culture medium was then replaced with culture medium containing or not containing (vehicle) odiparcil at various concentrations (0.03, 0.1, 0.3, 1, 3, or 10 µM), and then the cells were incubated for 72 h. After incubation, culture media were discarded and the cells were rinsed with PBS, then fixed in PFA 4%. A part of the wells was then incubated for 2 hours at 37° C. with an enzymatic solution of chondroitinase ABC (CSase). After 2 hours of digestion with CSase ABC buffers were discarded, then the cells were rinsed with PBS and permeabilized with PBS-Triton 0.1%. The cells were then labeled using a primary anti-chondroitin sulfate antibody. After 2 hours of incubation, the primary antibody was then revealed using a fluorescent secondary antibody (Alexa 488) and the cell nuclei were stained using Hoechst 33258 solution (bis-benzimide) in parallel.

Figure 3:
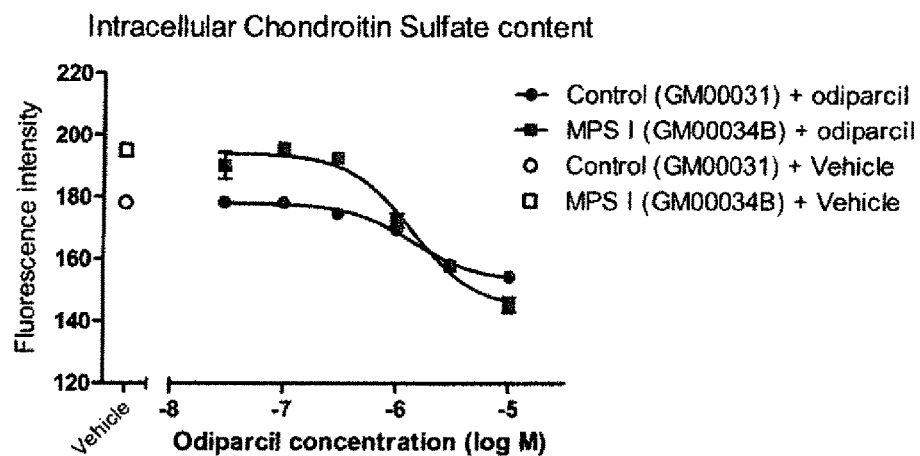
FIG. 3 shows the effect of odiparcil on intracellular chondroitin sulfate content in fibroblasts from MPS I patients.

As can be seen in FIG. 3, odiparcil inhibited, in a dose-dependent manner, intracellular chondroitin sulfate (CS) content in both control and MPS I fibroblasts. In both cell types odiparcil demonstrated a complete reduction of intracellular CS with $IC_{50}$s in the µM range.

These results demonstrate that odiparcil decreases intracellular chondroitin sulfate storage in fibroblasts from MPS I patients.

b) Effect on Chondroitin Sulfate, Dermatan Sulfate, and Heparan Sulfate in Human Fibroblasts from MPS I and MPS II Patients Human dermal fibroblasts (GM00034B and GM01391 fibroblast cells, isolated from two MPS I patients and GM03181 and GM00615 fibroblasts isolated from two MPS II patients) were obtained from the Coriell Institute for Medical Research. Cells were cultured in T25-flask for 24 h. The culture medium was then replaced with culture medium containing or not containing (vehicle) odiparcil at 10 µM, and then the cells were incubated for 72 h. After incubation, culture media were discarded and the cells were rinsed with PBS, then scrapped in PBS. Cells were then collected by centrifugation and cell pellets were frozen until further analysis. Quantitation of Heparan sulfate (HS), Dermatan sulfate (DS) and Chondroitin sulfate (CS) were performed using UPLC MSMS using a method adapted from method published in Zhang et al. 2015. Glycosaminoglycan values are expressed as mean+SD in µg GAG species per milligram protein.

Figures 4A, 4B:
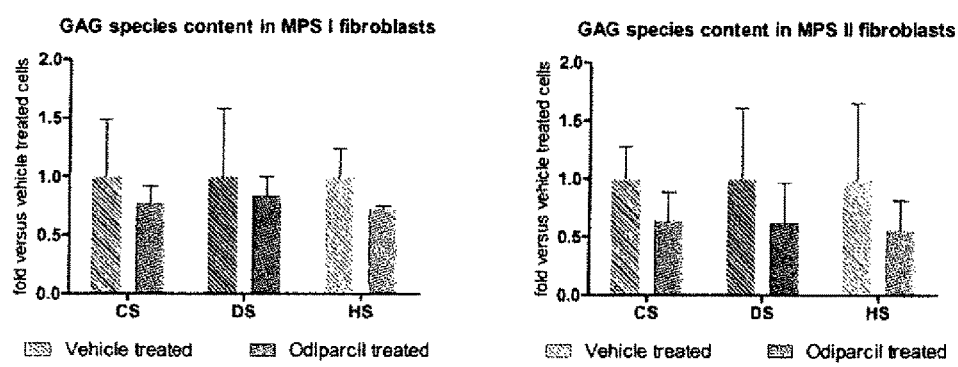
FIGS. 4A and 4B shows the effect of odiparcil on chondroitin sulfate, dermatan sulfate, and heparan sulfate in fibroblasts from MPS I and MPS II patients.

As can be seen in FIGS. 4A and 4B, odiparcil inhibited chondroitin sulfate (CS), dermatan sulfate (DS) and heparan sulfate (HS) content in both MPS I and MPS II fibroblasts. These results demonstrate that odiparcil decreases CS, DS, and HS storage in fibroblasts from MPS I and MPS II patients.

Example 2: Results Obtained In Vivo in Rabbits After Oral Administration

Odiparcil was administered Orally to New Zealand Rabbits at the Dose of 400 mg/kg. 4 h after the administration, the animals were anesthetized and blood samples were taken on citrate tubes after catherization of the carotid artery. After centrifugation, the plasma was removed and frozen. The plasma GAGs were isolated after digestion of the proteins with Pronase E, for 48 h at 50° C. The proteins and the protein residues were precipitated by adding trichloroacetic acid and incubated overnight at 4° C. After centrifugation, the supernatants were collected, and then dialyzed against 100 volumes of phosphate buffer, for 48 h at 4° C. A solution of cetylpyridinium chloride (0.1% final concentration) was added to the dialysates in order to precipitate the GAGs, for 24 h at ambient temperature. The samples were then centrifuged and the supernatant was removed. The precipitate obtained was redissolved in 2M sodium chloride and the GAGs were precipitated with 5 volumes of 95% ethanol. After centrifugation, the alcoholic precipitates were redissolved in 0.9% sodium chloride and desalified on a Sephadex G25 column (PD10).

The plasma GAGs extracted were quantified by assaying the uronic acid content, modified Bitter and Muir carbazole method. The qualitative analysis of the plasma GAG extracts was carried out by HPLC of the disaccharides obtained after enzymatic digestion with chrondroitinase ABC from *Proteus vulgaris* and chrondroitinase AC from *Arthrobacter aurescens*.

The table below shows that the treatment of the animals with odiparcil at the dose of 400 mg/kg increases by a factor of 5 the plasma GAG level (measured via the uronic acid content) compared with the control animals. From a qualitative point of view, the chondroitin-type GAGs experience an increase in their galactosamine-6-sulfate component and also in the dermatan sulfate component (chondroitin B), measured via the galactosamine-4-sulfate disaccharides (Δdi-4S DS).

|  | µg UA/ml plasma | Δdi-0S (%) | Δdi-4S (%) | Δdi-6S (%) | Δdi-UA2S (%) | Δdi-4S DS (%) |
|---|---|---|---|---|---|---|
| Control | 2.1 | 51.1 | 45.8 | 3.1 | 0 | 0 |
| Odiparcil | 11.4 | 18.6 | 26 | 30.8 | 4.1 | 20.5 |

UA: Uronic acid
Δdi-0S: nonsulfated disaccharides
Δdi-4S: 4-sulfated disaccharides
Δdi-6S: 6-sulfated disaccharides (galactosamine-6-sulfate component)
Δdi-UA2S: 2UA-sulfated disaccharides
Δdi-4S DS: 4-sulfated disaccharides (dermatan sulfate component)

These results demonstrate that odiparcil has the capacity to increase the synthesis of total GAGs (human fibroblasts), to increase the concentration of extracellular GAGs of chondroitin type (bovine aortic endothelial cells) and to increase the synthesis of plasma GAGs, in particular for GAGs of chondroitin type. It being understood that MPS type III, VI and VII are characterized by an accumulation of intracellular GAGs, these results indicate that odiparcil has the capacity to decrease the intracellular GAG load and therefore to have beneficial effects in the treatment of said MPSs.

Example 3: Results Obtained In Vivo in a Mouse MPS Model

The effect of odiparcil on GAG storage was assessed in a model of mucopolysaccharidosis induced by Tilorone.

Chronic administration of tilorone induces GAGs accumulation in various organs including liver, spleen, and kidney (Fischer et al. 1996, 315 (Pt 2):369-375; Prokopek 1991, 42:2187-2191). Tilorone (50 mg/kg/day) was administered via drinking water and odiparcil at 30 or 100 mg/kg/day (corresponding to 15 mg/kg and 50 mg/kg given bid, respectively) was given by oral gavage. Tilorone, odiparcil or vehicle were administered to male C57B16/J mice for 28 days.

After 21 days of treatment, urine were collected over a 24 hour period by placing the animal in diuresis/metabolic cages. The activity of odiparcil was assessed by quantifying total sulfated GAG levels in the collected urine. After a 10 to 20 fold dilution of the urine in water, sulfated glycosaminoglycan concentrations were measured using Blyscan™ assay from Biocolor (UK) following the manufacturer's instructions. Creatinine levels were also assessed on undiluted urine samples, using the CREATININE (Jaffé) kit (ref 981811) from ThermoFisher according to the manufacturer's instructions. Urinary sulfated GAG levels were normalized by creatinine levels. The data were analyzed statistically by one-way analysis of variance followed by a Tukey's test between all groups: ***: $p<0.001$ for vehicle/vehicle, and $\$\$\$$: $p<0.001$ for tilorone/vehicle.

Figure 5:
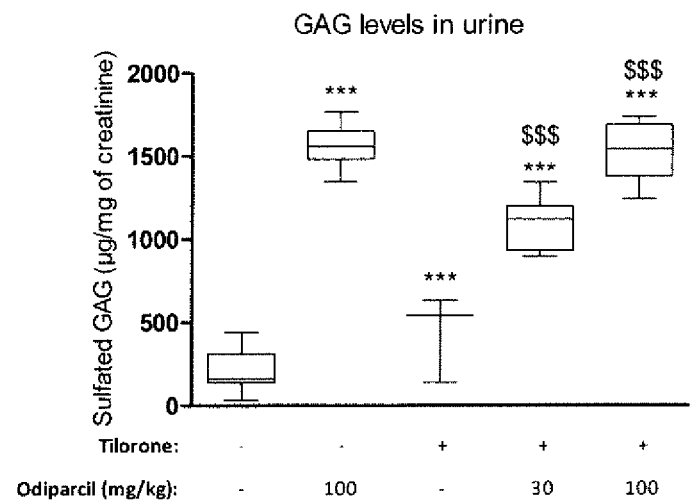
FIG. 5 shows the effect of odiparcil on GAG levels in urine in a tilorone-induced mucopolysaccharidosis mouse model.

The results of this study are shown in FIG. 5. Tilorone increased GAG levels in urine. Odiparcil administered concomitantly with tilorone increased sulfated GAG levels in urine in a dose-dependent manner; the effect of odiparcil was statistically significant at both tested doses.

These results demonstrate that odiparcil induces the excretion of GAG in urine in a tilorone-induced mucopolysaccharidosis mouse model.

At the end of the study period, animals were anesthetized and sacrificed. The liver of each animal was then collected, rinsed in physiological serum, blotted in absorbent paper and weighted. It was then cut in pieces and cooled by snap-freezing in liquid nitrogen before being stored at −80° C. The activity of odiparcil was assessed by quantifying total sulfated glycosaminoglycan (GAG) levels in the liver. Sulfated glycosaminoglycan concentration was measured using the Blyscan™ assay from Biocolor (UK) following the manufacturer's instructions. The data were statistically analyzed by one-way analysis of variance followed by a Tukey's test between all groups: ***: $p<0.001$ vs vehicle/vehicle, and $: $p<0.05$ vs tilorone/vehicle.

Figure 6:
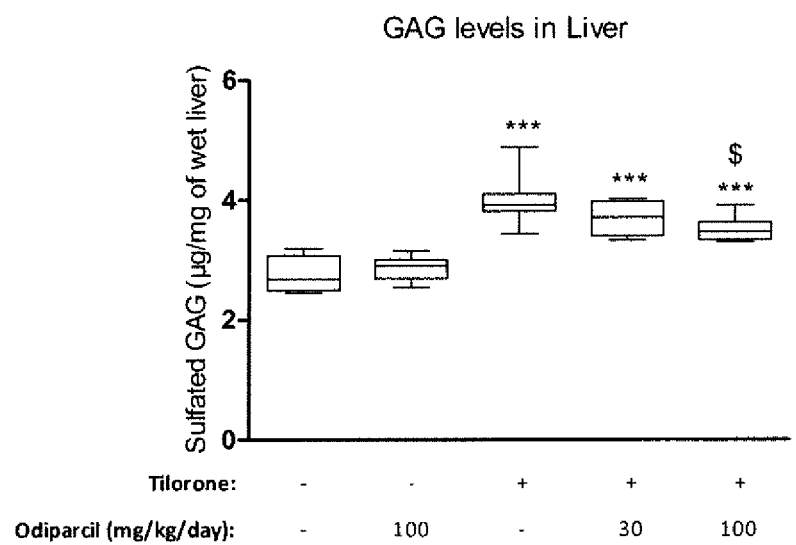
FIG. 6 shows the effect of odiparcil on GAG storage in liver in a tilorone-induced mucopolysaccharidosis mouse model.

The results of this study are shown in FIG. 6. Tilorone, as reported in the literature, increased GAG levels in the liver. Odiparcil administered concomitantly with tilorone for 4 days decreased the tilorone-induced accumulation of liver total GAG levels. The effect of odiparcil on total GAG liver content was statistically significant at the dose of 100 mg/kg/day).

These results demonstrate that odiparcil decreases GAG storage in a tilorone-induced mucopolysaccharidosis mouse model.

Example 4: Pharmaceutical Formulation

Tablet obtained by means of a wet granulation process, containing (in weight %):

| | |
|---|---|
| Odiparcil | 90% |
| Microcrystalline cellulose (NF or Ph Eur) | 7% |
| Povidone or polyvinylpyrrolidone (USP or Ph Eur) | 3% |
| Water (USP or Ph Eur) | qs for wet granulation |

The invention claimed is:

1. A method of treatment of a mucopolysaccharidosis type I or II, which comprises administering to a subject in need thereof a therapeutically effective amount of odiparcil (4-methyl-2-oxo-2H-1-benzopyran-7-yl-5-thio-β-D-xylopyranoside).

2. The method of claim 1, which comprises the daily administration of from about 100 mg to about 5000 mg of odiparcil.

3. The method of claim 1, wherein odiparcil is administered orally.

4. The method of claim 3, wherein odiparcil is administered with food.

5. The method of claim 1, for the treatment of mucopolysaccharidosis type I.

6. The method of claim 1, for the treatment of mucopolysaccharidosis type II.

7. A method of treatment of a mucopolysaccharidosis type I or II, which comprises administering to a subject in need thereof a pharmaceutical composition containing a therapeutically effective amount of odiparcil (4-methyl-2-oxo-2H-1-benzopyran-7-yl-5-thio-β-D-xylopyranoside).

8. The method of claim 7, wherein the pharmaceutical composition contains from about 100 mg to about 1000 mg of odiparcil.

9. The method of claim 7, wherein the pharmaceutical composition is an oral pharmaceutical form.

10. The method of claim 9, wherein the pharmaceutical composition is a solid formulation.

11. The method of claim 7, wherein odiparcil is administered with food.

12. The method of claim 7, for the treatment of mucopolysaccharidosis type I.

13. The method of claim 7, for the treatment of mucopolysaccharidosis type II.

14. A method for the treatment of a mucopolysaccharidosis in which an accumulation of chondroitin sulfate and/or dermatan sulfate occurs, which comprises administering to a subject in need thereof a therapeutically effective amount of odiparcil (4-methyl-2-oxo-2H-1-benzopyran-7-yl-5-thio-β-D-xylopyranoside).

15. The method of claim 14, which comprises the daily administration of from about 100 mg to about 5000 mg of odiparcil.

16. The method of claim 14, wherein odiparcil is administered orally.

17. The method of claim 16, wherein odiparcil is administered with food.

* * * * *

UNITED STATES PATENT AND TRADEMARK OFFICE
CERTIFICATE OF CORRECTION

PATENT NO. : 10,092,540 B2  
APPLICATION NO. : 15/420135  
DATED : October 9, 2018  
INVENTOR(S) : Masson et al.

Page 1 of 1

It is certified that error appears in the above-identified patent and that said Letters Patent is hereby corrected as shown below:

On the Title Page

Item [30], delete "FR 13 59659" and insert --FF 13 59657--

Signed and Sealed this
Eleventh Day of December, 2018

Andrei Iancu
*Director of the United States Patent and Trademark Office*